United States Patent [19]

Zoller et al.

[11] Patent Number: 5,290,947
[45] Date of Patent: Mar. 1, 1994

[54] PROCESS FOR THE PREPARATION OF PYRROLE DERIVATES

[75] Inventors: Gerhard Zoller, Schöneck; Eckard Kujath, Maintal; Klaus Delpy, Dietzenbach; Manfred Schrod, Weiterstadt, all of Fed. Rep. of Germany

[73] Assignee: Cassella Aktiengesellschaft, Frankfurt am Main, Fed. Rep. of Germany

[21] Appl. No.: 33,232

[22] Filed: Mar. 16, 1993

[30] Foreign Application Priority Data

Apr. 6, 1992 [DE] Fed. Rep. of Germany ....... 4211531

[51] Int. Cl.$^5$ ............ C07D 207/323; C07D 207/325; C07D 207/327
[52] U.S. Cl. .................................... 548/530
[58] Field of Search ......................... 548/530

[56] References Cited

U.S. PATENT DOCUMENTS

| | | | |
|---|---|---|---|
| 4,002,643 | 1/1977 | Carson | 260/326.5 |
| 4,792,568 | 12/1988 | Auerbach | 514/423 |
| 4,837,225 | 6/1989 | Zoller et al. | 514/427 |
| 4,996,901 | 10/1990 | Zoller et al. | 514/211 |
| 5,043,348 | 8/1991 | Zoller et al. | 514/423 |

OTHER PUBLICATIONS

March, "Advanced Organic Chemistry", 2nd Ed. (1977) p. 493; McGraw-Hill.
Hinman et al., "Methylpyrrols-Synthesis and Characterization", Journal of Organic Chem., vol. 28 (1963), pp. 3052-3058.

*Primary Examiner*—Joseph Paul Brust
*Attorney, Agent, or Firm*—Perman & Green

[57] ABSTRACT

The present invention relates to a process for the preparation of pyrrole derivatives of the general formula I

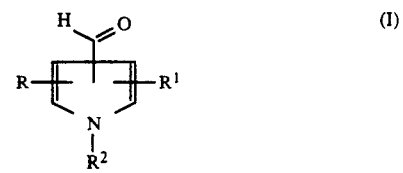

by reaction of a compound of the general formula III

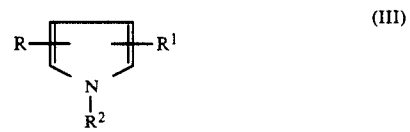

where R, R$^1$ and R$^2$ are defined as specified in claim 1, in a Vilsmeier reaction. The reaction is carried out in an easily degradable solvent, the reaction product is isolated with the aid of a water-miscible extractant and is purified by high-vacuum distillation in the short path evaporator.

8 Claims, No Drawings

PROCESS FOR THE PREPARATION OF PYRROLE DERIVATES

BACKGROUND OF THE INVENTION

1. Field of the Invention

The present invention relates to a process for the preparation of pyrrolaldehydes by Vilsmeier synthesis and purification by high-vacuum distillation. Pyrrolaldehydes are valuable pharmacologically active compounds and are described, for example, in EP-A 287 988 and corresponding U.S. Pat. No. 5,043,348. A Vilsmeier synthesis for the preparation thereof is also already specified there.

2. Discussion of Prior Art

The synthesis of relatively large amounts of substances by the Vilsmeier process poses problems with regard to industrial practicability. Moreover, on an industrial scale, the yields are relatively low and the purities of the products do not correspond to the requirements which must be made of a pharmacological active compound. Since, in the reaction itself, large amounts of halogen-containing solvents must be used, there are, in addition, considerable problems in keeping the waste water and exhaust air clean, and also with regard to the general safety at work. The purification of the products by repeated recrystallisation is associated with considerable losses of yield and the use of relatively large amounts of solvent.

SUMMARY OF THE INVENTION

The present invention therefore provides a process which supplies pyrrolaldehydes, even on an industrial scale, in good yields and in the purities required and is also as ecologically unobjectionable as possible.

This is surprisingly achieved according to the present invention by a process for the preparation of pyrrole derivatives of the general formula I

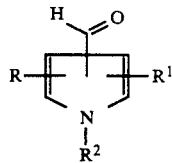

(I)

in which R and $R^1$, independently of each other, denote hydrogen or $(C_1-C_4)$-alkyl; $R^2$ denotes $(C_1-C_3)$-alkyl which is substituted by $-NH_2$, acylamino of the general formula II

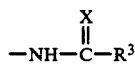

(II)

formyl, mono- or di-$(C_1-C_4)$-alkoxymethyl, $(C_1-C_4)$-alkoxycarbonyl or cyano; X denotes an oxygen or sulphur atom; and $R^3$ denotes hydrogen, unsubstituted or substituted $(C_1-C_5)$-alkyl, $(C_5-C_7)$-cycloalkyl, unsubstituted or substituted phenyl or phenylamino, amino or unsubstituted or substituted $(C_1-C_5)$-alkylamino, by reaction of a compound of the general formula III

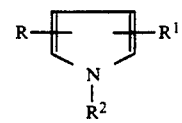

(III)

in which R, $R^1$ and $R^2$ are defined as specified above, in a Vilsmeier reaction, characterised in that the reaction is carried out in an easily degradable solvent, the reaction product is isolated with the aid of a water-miscible extractant and is purified by high-vacuum distillation in the short path evaporator.

Alkyl, alkoxy and alkylamino groups mentioned in the above definitions can be straight-chain or branched. Alkyl groups are, for example, methyl, ethyl, propyl and butyl. The same applies to alkoxy and alkylamino. $(C_5-C_7)$-Cycloalkyl is, in particular, cyclopentyl, cyclohexyl and cycloheptyl. The formyl group can be in the 2- or 3-position of the pyrrole ring. R and $R^1$ preferably denote hydrogen or methyl. X preferably denotes oxygen. Alkyl or alkylamino representing $R^3$ preferably has 1 or 2 C atoms. It can be unsubstituted or substituted by amino, mono- or di-$(C_1-C_4)$alkylamino or phenoxy.

Phenyl or phenylamino representing $R^3$ can be substituted by up to three substituents. Suitable substituents are, in particular, chlorine $(C_1-C_2)$-alkyl, $(C_1-C_2)$-alkoxy, $(C_1-C_2)$-alkoxycarbonyl and carboxyl.

Preferred radicals $R^2$ are $(C_1-C_3)$-alkyl radicals which are substituted by acetylamino, propionylamino, isopropionylamino, 4-chlorobenzoylamino, 4-chlorophenylaminocarbonylamino, cyanopropyl or 2,2-diethoxyethyl.

The process according to the invention can be carried out using all the reagents conventional in the Vilsmeier synthesis and disclosed in the literature (Houben-Weyl, Methoden der organischen Chemie [Methods in organic chemistry], 4th edition, E 3, pp. 16ff, 1983). However, preference is given to the process which employs dimethylformamide and phosphoryl chloride. The hydrolysis of the Vilsmeier complex is likewise performed in a known manner, for example using sodium hydroxide solution.

Preferred easily degradable solvents in which the process according to the invention is carried out are, for example, 1,2-dimethoxyethane, tetrahydrofuran, dioxan and diethylene glycol dimethyl ether.

When, for example, 6 normal sodium hydroxide solution is used for the hydrolysis of the Vilsmeier complex, the proportion of 1,2-dimethoxyethane can be varied in the range from 10 to over 100% by volume, based on the sodium hydroxide solution, a proportion of 40 to 80% by volume being particularly preferred.

Preferred water-miscible extractants which are used to isolate the pyrrole derivatives are 1,2-dimethoxyethane and tetrahydrofuran.

In a particularly preferred embodiment of the process according to the invention, during the hydrolysis of the Vilsmeier complex, the reaction mixture is pumped in circulation via an external cooling device.

By this means it is possible to avoid too intense a heating of the reaction mixture, owing to the highly exothermic reaction, and thus to minimise the proportion of by-products.

By high-vacuum distillation in the short path evaporator with a very good vacuum, it is possible to isolate the sensitive pyrrole derivatives without decomposition in good yield and purity.

The process according to the invention, even on an industrial scale, delivers pyrrole derivatives of the general formula I in good yields and high purity and is ecologically acceptable. It is thus considerably superior in every aspect to the known preparation processes and represents an unforeseeable enrichment of the art.

EXAMPLE 1

N-(2-(3-formyl-2,5-dimethyl-1H-pyrrolyl)ethyl)acetamide 123 ml (1.34 mol) of phosphoryl chloride are added dropwise in the course of 30 minutes at 0° C. to 750 ml of 1,2-dimethoxyethane and 109 ml of dimethyl formamide. The mixture is stirred for a further 30 minutes at 0° C., and, in the course of 45 minutes at 0° C., 180 g (1 mol) of N-(2-(2,5-dimethyl-1H-pyrrolyl)ethyl)acetamide are introduced. After 10 minutes at 0° C., the mixture is allowed to warm to 10° C., stirred for 1 h at 10° C. and hydrolysed by pouring in a solution of 250 g of sodium hydroxide in 920 ml of water in the course of 2 h at 20° C. to the reaction mixture. The resulting reaction mixture is filtered, the organic phase is isolated and the water phase is extracted twice, each time with 370 ml of 1,2-dimethoxyethane. The organic phases are combined and substantially concentrated in vacuum. After addition of 250 ml of toluene, the mixture is concentrated to dehydrate it, 1 l of ethyl acetate is added and the mixture is filtered over silica gel and charcoal, crystallised and dried.

Yield: 166 g (80%)

Melting point: 115°–117° C.

For further purification, the crude product was distilled in a high-vacuum apparatus at a vacuum of $<<10^{-3}$ mbar and a bath temperature of 220°–240° C. and recrystallised from 360 ml of 1,2-dimethoxyethane.

Yield: 155 g (74.7%)

Melting point: 118°–119° C.

Boiling point: 190°–195° C./$<10^{-3}$ mbar

Purity: >99.9% (HPLC, TLC)

Elemental analysis: $C_{11}H_{16}N_2O_2$ (208, 26): Calculated: C 63.4, H 7.7, N 13.5, O 15.4; Found: C 63.3, H 7.7, N 13.5, O 15.4.

The same procedure was carried out on a 30-fold greater scale with the corresponding result.

EXAMPLE 2

Analogously with Example 1, the reaction was carried out in tetrahydrofuran as solvent.

Yield: 77%

EXAMPLE 3

Analogously to Example 1, the reaction was carried out in diethylene glycol dimethyl ether as solvent.

Yield: 70%

EXAMPLE 4

1-(2,2-Diethoxyethyl)-2,5-dimethylpyrrol-3-aldehyde

The compound was obtained by analogy with Example 1 by formylation of 1-(2,2-diethoxyethyl)-2,5-dimethylpyrrole and purified by high-vacuum distillation.

Melting point: 109°–111° C.

Boiling point: 175°–180° C./$<10^{-3}$ mbar

It is to be understood that the above described embodiments of the invention are illustrative only, and that modifications thereof may occur to those skilled in the art. Accordingly, this invention is not to be regarded as limited to the embodiments disclosed herein, but is to be limited only as defined by the appended claims.

We claim:

1. Process for the preparation of a pyrrole compound of the formula I

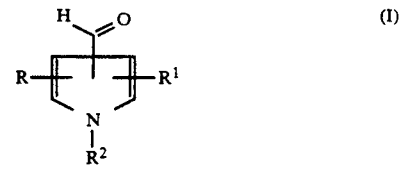

in which

R and $R^1$, independently of each other, denote hydrogen or $(C_1-C_4)$-alkyl;

$R^2$ denotes $(C_1-C_3)$-alkyl which is substituted by a radical selected from the group consisting of $-NH_2$, acylamino of the general formula II

formyl, mono- or di- $(C_1-C_4)$-alkoxymethyl, $(C_1-C_4)$-alkoxycarbonyl and cyano;

X denotes oxygen or sulphur; and $R^3$ denotes a radical selected from the group consisting of hydrogen, $(C_1-C_5)$-alkyl, $(C_5-C_7)$-cycloalkyl, phenyl or phenylamino, amino and $(C_1-C_5)$-alkylamino, by the Vilsmeier formylation reaction of a compound of the general formula III

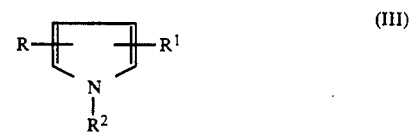

in which R, $R^1$ and $R^2$ are defined as specified above, with a disubstituted formamide and a catalyst in a degradable organic solvent, hydrolysing the reaction product to produce an organic solvent phase and an aqueous phase, both phases containing amounts of the desired formylated pyrrole derivative, separating the phases, extracting the formylated pyrrole derivative from the aqueous phase by means of a water-miscible organic extractant and adding it to the organic solvent phase, and purifying the formylated pyrrole derivative by high vacuum distillation of the organic solvent phase in a short path evaporator.

2. Process according to claim 1, characterised in that R and $R^1$, independently of each other, denote hydrogen or methyl.

3. Process according to claim 1, characterised in that X denotes oxygen.

4. Process according to claim 1, characterized in that $R^2$ denotes $(C_1-C_3)$-alkyl, which is substituted by a radical selected from the group consisting of acetylamino, propionylamino, isopropionylamino, 4-chlorobenzoylamino, 4-chlorophenylaminocarbonylamino, cyano-propyl and 2,2-diethoxyethyl.

5. Process according to claim 1, characterized in that the Vilsmeier reaction is carried out using dimethylformamide as the disubstituted formamide and phosphoryl chloride as the catalyst.

6. Process according to claim 1, characterized in that the organic solvent used is selected form the group consisting of 1,2-dimethoxyethane, tetrahydrofuran and diethylene glycol dimethyl ether.

7. Process according to claim 1, characterized in that the extractant used is selected from the group consisting of 1,2-dimethoxyethane and tetrahydrofuran.

8. Process according to claim 1, characterized in that, during the hydrolysis step, the reaction mixture is pumped in circulation via and external cooling device.

* * * * *